(12) United States Patent
Kato et al.

(10) Patent No.: US 7,511,026 B2
(45) Date of Patent: Mar. 31, 2009

(54) THERAPEUTIC AGENT FOR NERVE DAMAGE

(75) Inventors: Tadahiko Kato, Tokyo (JP); Akira Asari, Musashino (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 279 days.

(21) Appl. No.: 10/550,998

(22) PCT Filed: Mar. 25, 2003

(86) PCT No.: PCT/JP04/04240

§ 371 (c)(1),
(2), (4) Date: Oct. 24, 2005

(87) PCT Pub. No.: WO2004/084912

PCT Pub. Date: Oct. 7, 2004

(65) Prior Publication Data

US 2006/0135439 A1   Jun. 22, 2006

(30) Foreign Application Priority Data

Mar. 25, 2003   (JP) .............................. 2003-083831

(51) Int. Cl.
*A61K 31/728* (2006.01)
*A61K 31/715* (2006.01)

(52) U.S. Cl. ........................ 514/54; 514/23; 536/123.1; 536/124

(58) Field of Classification Search ................... 514/54, 514/23; 536/123.1, 124
See application file for complete search history.

(56) References Cited

U.S. PATENT DOCUMENTS

| 6,380,173 | B1 | 4/2002 | Stutzmann et al. |
| 2002/0040013 | A1 | 4/2002 | Stutzmann et al. |

FOREIGN PATENT DOCUMENTS

| CA | 2 414 211 | 1/2003 |
| EP | 0 582 330 | 2/1994 |
| EP | 1 059 304 | 1/2000 |
| FR | 2 800 074 | 4/2001 |
| FR | 2 807 043 | 10/2001 |
| JP | 06-157322 | 6/1994 |
| JP | 09-030979 | 2/1997 |
| JP | 09-227386 | 9/1997 |
| JP | 11-140103 | 5/1999 |
| JP | 11140103 A * | 5/1999 |
| JP | 11-310602 | 11/1999 |
| JP | 2000-198738 | 7/2000 |
| JP | 2002-29974 | 1/2002 |
| JP | 2002-500660 | 1/2002 |
| JP | 2002-265369 | 9/2002 |
| JP | 2003-119146 | 4/2003 |
| JP | 2004-075616 | 3/2004 |
| JP | 2004-75618 | 3/2004 |
| WO | WO 91/06303 | 5/1991 |
| WO | WO 00/44367 | 8/2000 |
| WO | WO 01/51003 | 7/2001 |
| WO | WO 01/72762 | 10/2001 |
| WO | WO 02/04471 | 1/2002 |
| WO | WO 02/04471 A1 * | 1/2002 |
| WO | WO 02/09728 | 2/2002 |
| WO | WO 01/29055 | 4/2002 |

OTHER PUBLICATIONS

Atsuta et al., JP 11140103 A (May 25, 1999 (Abstract Sent).*
Livant et al. (Carbohydrate Research (1992), 237, 271-81) (Abstract Sent).*
Supplementary Partial European Search Report dated Apr. 5, 2007.

* cited by examiner

*Primary Examiner*—Shaojia Anna Jiang
*Assistant Examiner*—Michael C Henry
(74) *Attorney, Agent, or Firm*—Knobbe, Martens, Olson & Bear, LLP

(57) ABSTRACT

The present invention provides a therapeutic agent for nerve damages such as those caused by spinal cord injury or nerve trauma, which includes, as an active ingredient, a low-molecular-weight saccharide composed of at least glucuronic acid and/or N-acetylglucosamine or a pharmaceutically acceptable salt thereof. The present invention also provides a therapeutic agent for nerve damages which includes, as an active ingredient, preferably a low-molecular-weight hyaluronic acid, more preferably hyaluronic acid disaccharide to hyaluronic acid 2,500-saccharide, further more preferably hyaluronic acid disaccharide to hyaluronic acid 50-saccharide, much more preferably hyaluronic acid tetrasaccharide, or a pharmaceutically acceptable salt thereof.

8 Claims, 13 Drawing Sheets

US 7,511,026 B2

THERAPEUTIC AGENT FOR NERVE DAMAGE

RELATED APPLICATIONS

This application is the U.S. National Phase under 35 U.S.C. §371 of International Application PCT/JP2004/004240, filed Mar. 25, 2004, which was published in a language other than English, which claims priority of Japanese Patent Application No. 2003-083831, filed Mar. 25, 2003.

TECHNICAL FIELD

The present invention relates to a therapeutic agent for nerve damage which comprises, as an active ingredient, a low-molecular-weight saccharide composed of at least glucuronic acid and/or N-acetylglucosamine (in particular, a low-molecular-weight hyaluronic acid) or a pharmaceutically acceptable salt thereof.

BACKGROUND ART

JP 11-140103A discloses an aqueous solution containing hyaluronic acid (HA) or a pharmaceutically acceptable salt thereof for spinal cord perfusion, and it describes that the solution for perfusion may be used in the spinal cord perfusion therapy for spinal cord injury. In addition, HA having average molecular weight of 500,000 to 4,000,000 is exemplified in the document.

However, there is no disclosure or suggestion about use of a low-molecular-weight saccharide (in particular, a low-molecular-weight HA) composed of at least glucuronic acid (GlcA) and/or N-acetylglucosamine (GlcNAc), and therefore there is no disclosure or suggestion that such a low-molecular-weight saccharide brings about a more excellent effect.

DISCLOSURE OF THE INVENTION

First, abbreviations used in the present description will be described.
GlcNAc: N-acetylglucosamine
GlcA: glucuronic acid
HA: hyaluronic acid
DMSO: dimethylsulfoxide
PBS: phosphate buffered saline
SCEP: spinal cord evoked potential An object of the present invention is to provide a safe and useful therapeutic agent for nerve damage which comprises, as an active ingredient, a low-molecular-weight saccharide composed of at least GlcA and/or GlcNAc (in particular, a low-molecular-weight HA) or a pharmaceutically acceptable salt thereof.

The inventors of the present invention have made extensive studies to solve the above-described problems and found that a low-molecular-weight saccharide composed of at least GlcA and/or GlcNAc (in particular, a low-molecular-weight HA) exerts an extremely excellent effect on nerve damage, in particular, on spinal cord injury. Thus, they have provided a therapeutic agent for nerve damage capable of solving the above-described problems and have achieved the present invention.

That is, the present invention provides a therapeutic agent for nerve damage (hereinafter, referred to as the therapeutic agent of the present invention) comprising, as an active ingredient, a low-molecular-weight saccharide composed of at least GlcA and/or GlcNAc or a pharmaceutically acceptable salt thereof.

The "low-molecular-weight saccharide composed of at least GlcA and/or GlcNAc" used herein is preferably a low-molecular-weight HA. Meanwhile, the "low-molecular-weight HA" is preferably HA disaccharide to HA 2,500-saccharide, more preferably HA disaccharide to HA 50-saccharide, particularly preferably HA tetrasaccharide.

The therapeutic agent of the present invention is preferably a therapeutic agent for spinal cord injury or nerve trauma.

The present invention also provides a method of treating nerve damage, comprising administering an effective amount of a low-molecular-weight saccharide composed of at least GlcA and/or GlcNAc or a pharmaceutically acceptable salt thereof to an animal suffering from nerve damage (in particular, mammals including human).

The present invention also provides a use of a low-molecular-weight saccharide composed of at least GlcA and/or GlcNAc or a pharmaceutically acceptable salt thereof in manufacturing a therapeutic agent for nerve damage.

illustrate results of balance beam crossing and metal gauze crossing, respectively. The symbols "***" in this graphs represent the significant difference of p<0.0001 against the physiological saline-administered group (Tukey's multiple comparison test).

Figure 13:
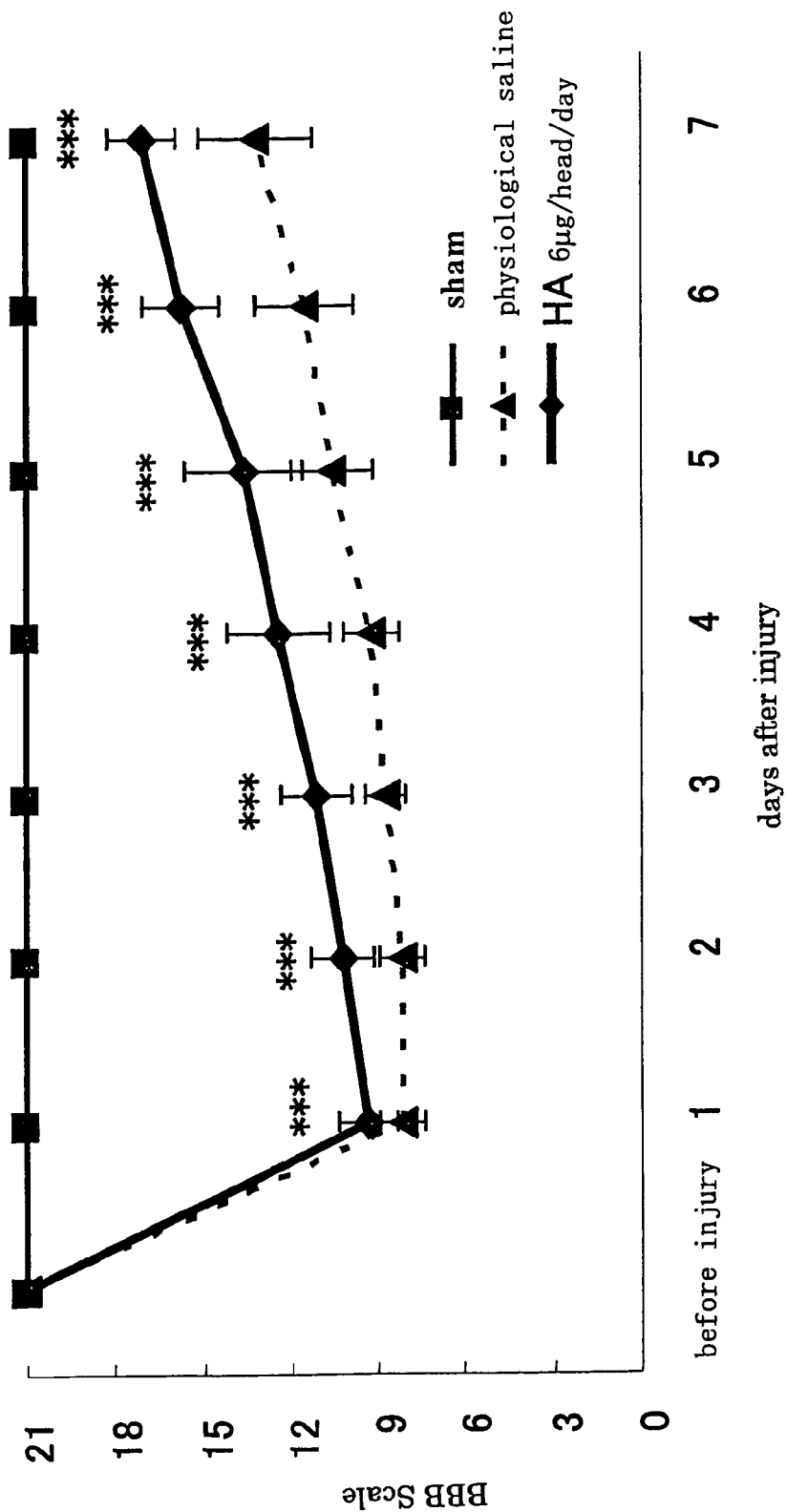

FIG. 13 is a graph illustrating measurement results (BBB scale) of the motor function tests for 7 days after the spinal cord injury in the hind limb in severely injured models (II). The symbols "***" in this graph represent the significant difference of p<0.0001 against the physiological saline-administered group (Tukey's multiple comparison test).

DESCRIPTION OF THE PREFERRED EMBODIMENTS

The present invention will be described below in detail.

<1> Active Ingredient in the Therapeutic Agent of the Present Invention (1) Low-Molecular-Weight Saccharide Composed of at Least GlcA and/or GlcNAc or a Pharmaceutically Acceptable Salt Thereof In the present description, the "low-molecular-weight saccharide composed of at least GlcA and/or GlcNAc" includes "low-molecular-weight saccharide composed of at least GlcA", "low-molecular-weight saccharide composed of at least GlcNAc", and "low-molecular-weight saccharide composed of at least GlcA and GlcNAc". The "low-molecular-weight saccharide composed of at least GlcA" includes "GlcA" as a monosaccharide, and the "low-molecular-weight saccharide composed of at least GlcNAc" includes "GlcNAc" as a monosaccharide.

GlcA is preferably D-glucuronic acid, and GlcNAc is preferably N-acetyl-D-glucosamine.

Such a "low-molecular-weight saccharide composed of at least GlcA and/or GlcNAc" is preferably a low-molecular-weight HA. In addition, such a low-molecular-weight saccharide preferably does not have a sulfate group.

In the present description, the "low-molecular-weight HA" is a low-molecular-weight sugar chain having a composition similar to a disaccharide composition of HA. Specifically, it means a low-molecular-weight sugar chain in which GlcA and GlcNAc are linked alternately via glycosidic bond.

As long as the low-molecular-weight HA is such a low-molecular-weight sugar chain, the "low-molecular-weight HA" used herein includes a sugar chain having a non-reducing end of GlcA as well as a sugar chain having a non-reducing end of GlcNAc. Of those, a sugar chain having GlcA as a monosaccharide located in the non-reducing end is preferable. Also, a sugar chain having GlcNAc as a monosaccharide located in the reducing end is preferable.

The monosaccharide located in the non-reducing end may be a saturated sugar (a monosaccharide containing no carbon-carbon double bond) or an unsaturated sugar (a monosaccharide containing a carbon-carbon double bond). Of those, a sugar chain having a saturated sugar as a monosaccharide located in the non-reducing end is preferable.

In the present description, the "low-molecular weight" means a molecular weight recognized as a low-molecular weight by a person skilled in the art (in particular, in the technical field related to glycosaminoglycan). A molecule having an average molecular weight of more than 1,000 kD is not recognized as a molecule having a "low-molecular weight" in the art.

The "low-molecular-weight HA" is preferably HA disaccharide to HA 2,500-saccharide, more preferably HA disaccharide to HA 2,000-saccharide, further more preferably HA disaccharide to HA 1,500-saccharide, much more preferably HA disaccharide to HA 1,000-saccharide, particularly preferably HA disaccharide to HA 500-saccharide, very particularly preferably HA disaccharide to HA 250-saccharide, extremely preferably HA disaccharide to HA 100-saccharide. Of those, HA oligosaccharide is extremely preferable.

Herein, the "oligosaccharide" means a sugar chain recognized as an oligosaccharide by a person skilled in the art. Examples of the "HA oligosaccharide" include HA disaccharide to HA 50-saccharide. The HA oligosaccharide is preferably HA disaccharide to HA 30-saccharide, more preferably HA disaccharide to HA 20-saccharide, further more preferably HA disaccharide to HA 10-saccharide, much more preferably HA tetrasaccharide.

The low-molecular-weight HA may be a mixture of saccharides having various molecular weights. Therefore, the above-described HA tetrasaccharide includes not only HA tetrasaccharide but also a mixture of HA oligosaccharides containing HA tetrasaccharide as a main component. The HA oligosaccharides used herein include the above-exemplified mixture of HA oligosaccharides.

The glycosidic bond between GlcA and GlcNAc is preferably a $\beta1 \rightarrow 3$ bond, and the glycosidic bond between GlcNAc and GlcA is preferably a $\beta1 \rightarrow 4$ bond.

The origin of the "low-molecular-weight saccharide composed of at least GlcA and/or GlcNAc or a pharmaceutically acceptable salt thereof" used in the therapeutic agent of the present invention is not particularly limited. For example, in the case that a low-molecular-weight HA is used as such a sugar chain, it may be produced by a method of decomposing HA isolated and purified from cock's comb, umbilical cord, HA-producing microorganisms or the like (for example, enzyme decomposition method, chemical decomposition method, heat treatment method, ultrasonic treatment method or the like) or by synthesis method (for example, chemical synthesis method or enzymatic synthesis method).

Examples of the enzyme decomposition method include a method of using an enzyme capable of decomposing HA such as hyaluronidase (derived from testis), hyaluronidase (derived from *Streptomyces*), hyaluronidase SD, chondroitinase ACI, chondroitinase ACII, chondroitinase ACIII, or chondroitinase ABC on HA (see Shin Seikagaku Jikken Koza (New Biochemical Experiment Course) "Sugars II—Proteoglycan and Glycosaminoglycan-" p 244-248, published in 1991, Tokyo Kagaku Dozin Co., Ltd., or Glycobiology, 12, p 421-426, 2002). In order to obtain the low-molecular-weight HA, HA hydrolase is preferably used as an enzyme capable of decomposing HA.

Examples of the chemical decomposition method include alkaline decomposition method and DMSO method or the like. The alkaline decomposition method may be performed by adding a base such as about 1N of sodium hydroxide to a HA solution, heating the mixture for several hours to yield a HA having a low molecular weight, and adding an acid such as hydrochloric acid to neutralize the solution. Examples of the DMSO method include a method described by Nagasawa et al. (Carbohyd. Res., 141, p 99-110, 1985). Examples of the ultrasonic treatment method include a method described in Biochem., 33, p 6503-6507 (1994) or the like.

Examples of the synthesis method include a method described in Glycoconjugate J., p 453-439 (1993), WO 93/20827 or the like.

A fraction containing a low-molecular-weight HA is obtained by those methods as described above, and the fraction may further be purified by general techniques for separating and purifying sugar chains. For example, the purification may be performed by adsorption chromatography, anion-exchange chromatography, hydrophobic chromatography, gel-filtration method, gel permeation chromatography, paper electrophoresis method, paper chromatography, dialysis, fractionation with an organic solvent, a combination thereof, or the like (Glycobiology, 12, p 421-426, 2002), but the purification method is not limited to these methods.

These methods make it possible to increase the content of the low-molecular-weight HA in a fraction and to avoid contamination of a substances undesirable for medicine.

The thus-obtained low-molecular-weight HA is preferably a highly purified HA which does not substantially contain a substance undesirable for medicine.

As a pharmaceutically acceptable salt of a low-molecular-weight saccharide composed of at least GlcA and/or GlcNAc, for example, a pharmaceutically acceptable salt selected from alkaline metal salts (such as sodium salt, lithium salt, and potassium salt), alkaline earth metal salts, an inorganic salt such as ammonium salt, or organic salts such as a diethanolamine salt, cyclohexylamine salt and amino acid salt may be used. Of those, a sodium salt is preferably used.

When the above-described low-molecular-weight saccharide composed of at least GlcA and/or GlcNAc or a pharmaceutically acceptable salt thereof is used, a therapeutic agent for nerve damage having an extremely excellent pharmacological effect can be obtained.

The endotoxin concentration in the low-molecular-weight saccharide composed of at least GlcA and/or GlcNAc or a pharmaceutically acceptable salt thereof used in the therapeutic agent of the present invention is preferably 0.3 EU/mL or less in the case that the therapeutic agent of the present invention is a liquid formulation. In the case that the therapeutic agent is other than a liquid formulation, the endotoxin concentration is preferably not more than the amount corresponding to the above-described endotoxin content in a liquid formulation. The endotoxin concentration in the therapeutic agent of the present invention may be determined using an endotoxin determination method that is well known to and commonly used by a person skilled in the art, but preferable is the *limulus* test method which can be performed by using a *limulus amebocyte* lysate ingredient. EU (endotoxin unit) may be determined and calculated according to the general rules for biochemical reagents in Japanese Industrial Standards (JIS K8008). Meanwhile, the iron content is preferably 20 ppm or less.

(2) Dosage Form or the Like of Therapeutic Agent of the Present Invention

The administration method of the therapeutic agent of the present invention is not particularly limited as long as the therapeutic agent of the present invention can exert an effect on nerve damage. Examples of administration routes include injection (intradural, intravenous, intramuscular, subcutaneous, intracutaneous, intraperitoneal, or the like), transnasal, oral, percutaneous, and inhalation. The administration method such as direct administration by injection to a certain site or drip administration is appropriately selected depending on a disease or a site to be applied. In the case of intradural administration or the like, an implantable pump for drug infusion may be implanted in the body to perform continuous administration.

Depending on such administration route or administration method, the above-described low-molecular-weight saccharide or a pharmaceutically acceptable salt thereof is appropriately formulated to prepare the therapeutic agent of the present invention. Examples of the dosage form include injections (such as solutions, suspensions, emulsions, and solid formulations to be dissolved before use), tablets, capsules, liquid formulations, granules, powders, lipo formulations, ointments, plasters, lotions, pastes, patches, gels, suppositories, powders for external use, sprays, and powders for inhalation. A form of a liquid formulation such as an injection is preferable.

The liquid formulation may be produced by dissolving a low-molecular-weight saccharide composed of at least GlcA and/or GlcNAc or a pharmaceutically acceptable salt thereof in, for example, an appropriate aqueous solvent or a solvent commonly used for drugs. Examples of such solvents include distilled water, buffers, physiological saline, and water containing a water-miscible organic solvent or the like.

In the case that the therapeutic agent of the present invention is provided as an injectable agent, its form may be a solution, frozen product, or freeze-dried product. The therapeutic agent is filled and sealed in an appropriate container such as an ampule, vial or syringe for injection, for distribution or preservation, and it may be administered as an injection.

For formulating the therapeutic agent of the present invention, a known method may be used. When the treatment agent is formulated, other active ingredients (such as anti-inflammatory drugs, analgesics, vitamin preparations, antibacterial agents, growth factors, and adhesion factors), or ingredients generally used in medicines such as conventional stabilizing agents, emulsifiers, osmotic regulators, pH regulators, buffers, tonicity agents, preservatives, soothing agents, colorants, diluents, binders, lubricants and disintegrators may be used, as long as those ingredients exert no unfavorable influence on the above-described saccharide or a pharmaceutically acceptable salt thereof and exert no influence on the effects of the present invention.

The therapeutic agent of the present invention comprises a low-molecular-weight saccharide composed of at least GlcA and/or GlcNAc or a pharmaceutically acceptable salt thereof as an active ingredient, so that the therapeutic agent has only to contain a low-molecular-weight saccharide composed of at least GlcA and/or GlcNAc or a pharmaceutically acceptable salt thereof, and may further contain saccharides having other molecular sizes or other species of saccharides.

(3) Subject to be Administered with the Therapeutic Agent of the Present Invention The therapeutic agent of the present invention is intended to treat nerve damage, so that it may be applied to animals in a condition where a treatment for nerve damage is desired, that is, to animals suffering from nerve damage.

The "condition where a treatment for nerve damage is desired" is not particularly limited, but examples thereof include spinal cord injury or nerve trauma such as head trauma, cerebral (infantile) paralysis, spinal vascular damage, cervical spondylosis, senile dementia, Alzheimer's disease, Parkinson's disease, and spinocerebellar degeneration (hereditary spastic paraparesis). Of those, the treatment agent is preferably applied to spinal cord injury or nerve trauma, more preferably to spinal cord injury. Examples of the spinal cord injury include traumatic spinal cord injury, vertebral degenerative disease (spondylosis or the like), vetevral inflammatory disease (spondylitis, chronic rheumatoid arthritis or the like), tumor (spinal cord tumor, vertebral tumor or the like), vascular disease (spinal cord bleeding, cerebral embolism, spinal paralysis caused by extramedullary vascular damage or the like), myelitis (arachnoiditis, viral myelitis bacterial myelitis, or the like), multiple sclerosis, and amyotrophic lateral sclerosis. In particular, the therapeutic agent is effective for traumatic spinal cord injury.

That is, the therapeutic agent of the present invention is preferably a therapeutic agent for spinal cord injury or nerve trauma, more preferably a therapeutic agent for spinal cord injury, particularly preferably a therapeutic agent for traumatic spinal cord injury.

In the case that the therapeutic agent of the present invention is administered to an animal, the animal to be administered with the treatment agent is preferably a vertebrate, particularly preferably mammals including human. The object of "treatment" performed by the therapeutic agent of the present invention is not particularly limited, but the object may be suppression of progression (prevention of deterioration), improvement of symptoms, or healing for nerve damage, or the like.

The blending amount, dose per administration, administration interval, and the like of the low-molecular-weight saccharide composed of at least GlcA and/or GlcNAc or a pharmaceutically acceptable salt thereof in the therapeutic agent of the present invention are not particularly limited and are individually determined depending on, for example, administration method, administration form, and intent of using the therapeutic agent of the present invention, specific symptom, age, sex, and weight of a patient. Examples of the clinical dose of a low-molecular-weight saccharide composed of at least GlcA and/or GlcNAc or a pharmaceutically acceptable salt thereof may be 100 μg to 1,000 mg per adult per administration.

The administration interval of the therapeutic agent of the present invention may be about once a day, or the agent may be administered twice to three times a day. Meanwhile, the agent may also be administered continuously using an implantable pump for drug infusion as described above.

In addition to the treatment agent of the present invention, the present invention also includes a method of treating nerve damage, comprising administering a low-molecular-weight saccharide composed of at least GlcA and/or GlcNAc or a pharmaceutically acceptable salt thereof to a subject (animal) that requires a treatment for nerve damage.

EXAMPLES

Hereinafter, examples of the present invention will specifically be described. However, the scope of the present invention is not limited thereto.

<Materials Etc.>

First, substances or the like used in the present examples will be described. Reagents etc.

A low-molecular-weight HA was used as a low-molecular-weight saccharide composed of at least GlcA and/or GlcNAc.

HA from Seikagaku Corporation was used as the low-molecular-weight HA. The low-molecular-weight HA had the following structure and had the following properties (abbreviations to be used in the present examples are shown in the following parentheses. In the following formula, the symbols "-" represent glycosidic bonds.).

saturated HA tetrasaccharide (hereinafter, referred to as "HA4").

GlcA-GlcNAc-GlcA-GlcNAc

HA4 was obtained by size-fractionation with anion-exchange chromatography of a degraded product obtained by treating HA with DMSO containing hydrochloric acid (HCl), according to the method described by Nagasawa et al. (Carbohyd. Res., 141, p 99-110, 1985).

HA4 was dissolved in PBS so as to have a predetermined concentration according to the following pharmacological test and used. All the endotoxin concentrations after HA4 had been dissolved in PBS were 0.3 EU/mL or less, whereas all the iron contents were 20 ppm or less.

Figure 1:
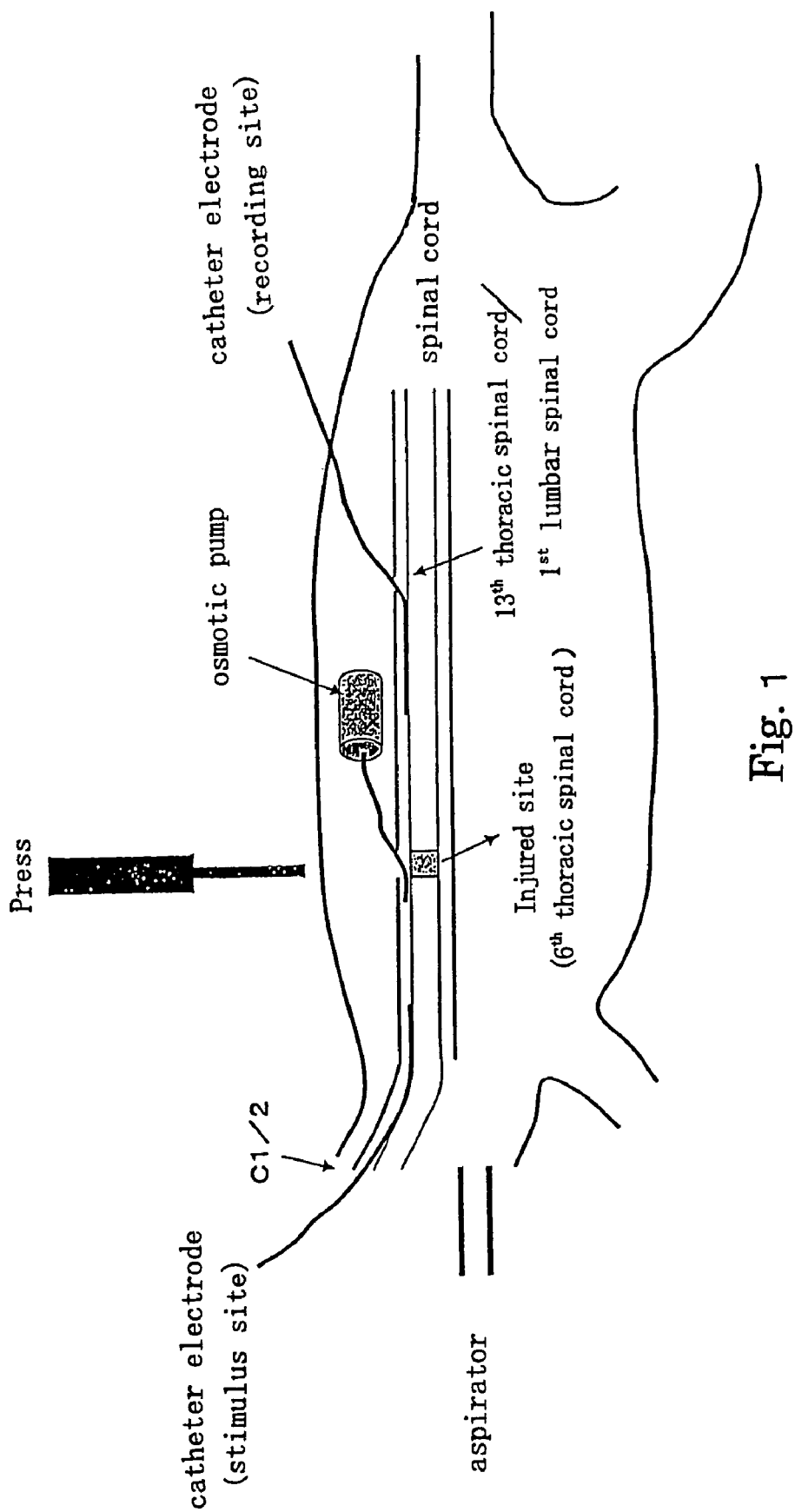
FIG. 1 is a scheme of a pharmacology test method.
Figure 2:
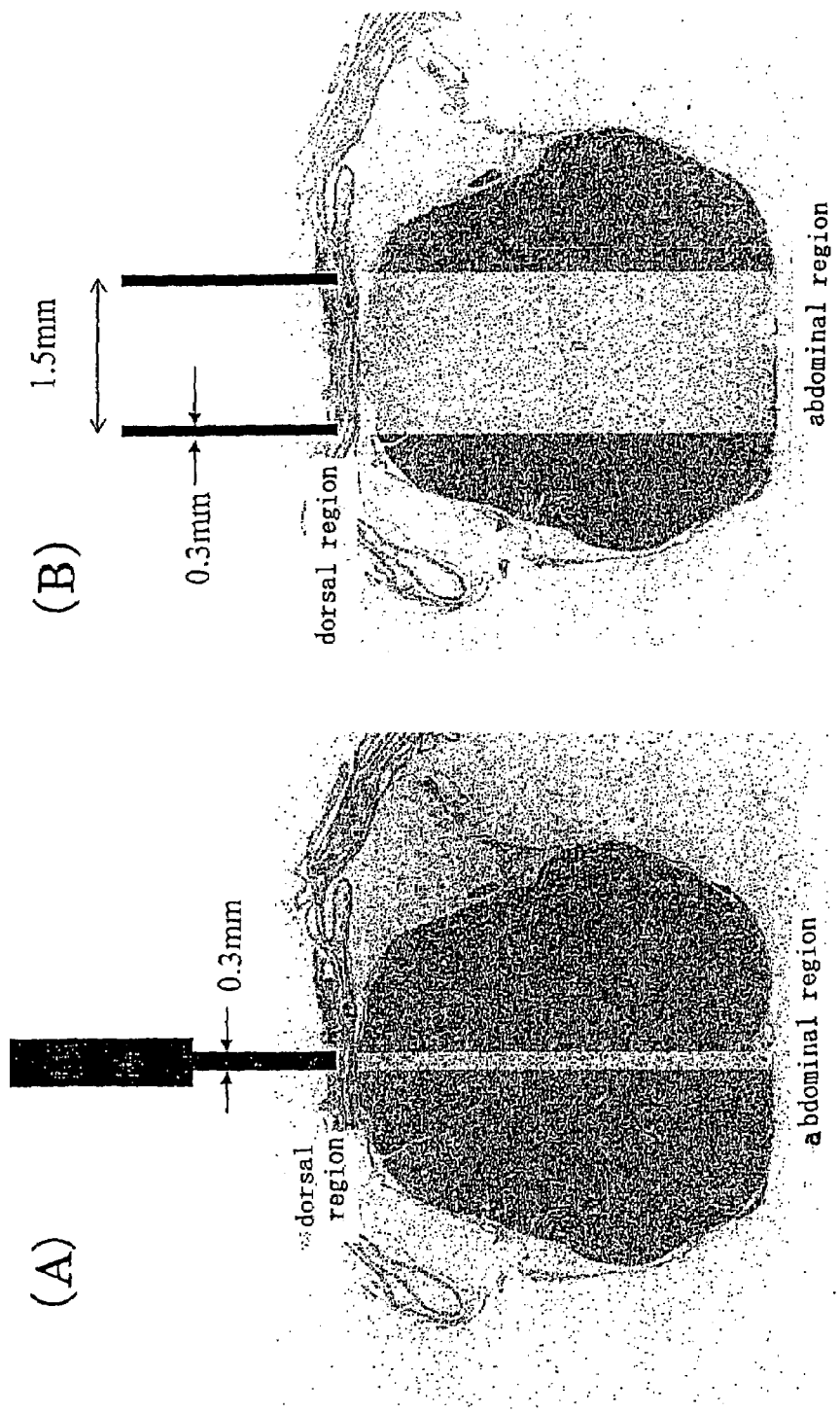
FIG. 2 is diagrams (photographs) illustrating degrees of injury in a slightly injured model (A) and a seriously injured model (I)(B).

<Pharmacology Test> Effect of HA4 on Spinal Cord Injury (1) Preparation of Spinal Cord Injury Model and Administration of HA4 (FIGS. 1 and 2)

FIG. 1 shows a scheme of the present test.

Wister rats (SPF, male) were used as animals, and each body was shaved from the neck to the hip using an electric hair clipper under pentobarbital (50 mg/kg weight) anesthesia and cleaned with 70% ethanol and Isodine (manufactured by Meiji Seika Kaisha, Ltd.). The dorsal skin was incised to expose thoracic vertebra from T5 to T10, and hemilaminectomy of the sixth thoracic vertebra (T6 thoracic vertebra) was performed to make a small incision in the dura mater, followed by regional anesthesia with xylocaine (manufactured by Astra Zeneca). Subsequently, two models were prepared as follows: a spatula (the tip of which had been processed into 0.3 mm) was inserted to the T6 position from the dorsal until the tip reached the abdominal centrum and maintained for 10 minutes to injure the spinal cord (slightly injured model), while a tweezer (the tip of which had been processed into 0.3 mm) was inserted until the tip reached the abdominal centrum, and the portion was pinched from both sides for 10 seconds to injure the spinal cord (seriously injured model). A respirator was used only when spinal cord evoked potentials were measured. The respirator was inserted into the windpipe under 1.0 to 2.0% halothane anesthesia and stabilized with a muscle relaxant. The damage degrees of the respective models were shown in FIG. 2.

After the injury, HA4 (6 μl) was immediately administered using a microsyringe (25 μl; manufactured by Ito Seisakusyo Co., Ltd.) into the dura mater. Thereafter, the tip (OD: 0.3 mm) of a tube that was filled with HA4 and connected with an osmotic pump (model 1002, manufactured by Alzet) was placed under the dura mater of the rostral in the injured portion, and HA4 was continuously administered for 7 days. Meanwhile, 5 minutes, 2 hours, 4 hours, and 6 hours after the injury, 30 mg/kg of methylprednisolone sodium succinate (MPSS, manufactured by Pharmacia) was administered into the tail vein as a positive control. For separating the injured portion from the surrounding tissues, a gelatin sponge (Gelform; manufactured by Pharmacia) was placed, and the rat was brought back to a feeding gauge after the wound had been sewn.

The group constitutions of the present test were as follows.
1. Slightly Injured Model:
    (1) No injury/No treatment group
    (2) PBS-administered group (physiological saline-administered group)
    (3) HA4 (60 μg/animal/day)-administered group
2. Seriously Injured Model (I):
    (1) No injury/No treatment group
    (2) PBS-administered group (physiological saline-administered group)
    (3) Methylprednisolone (MPSS; 30 mg/kg weight/day×4 times)-administered group
    (4) HA4 (0.6 μg/animal/day)-administered group
    (5) HA4 (6.0 μg/animal/day)-administered group
3. Seriously Injured Model (II):
    (1) Sham surgery group prepared by making a small incision in the dura mater (Sham)
    (2) PBS-administered group (physiological saline-administered group)
    (3) HA4 (6.0 μg/animal/day)-administered group (2) Evaluation on Performance Status After a test substance had been administered, the performance status was observed. As a result, for the PBS-administered group, difficulty in walking was observed even 7 days after the administration, while for the HA4-administrated group, walking approximately similar to that of the normal rat was observed.

(3) Influence of HA4 on spinal Cord Evoked Potential (SCEP)

Figure 3:
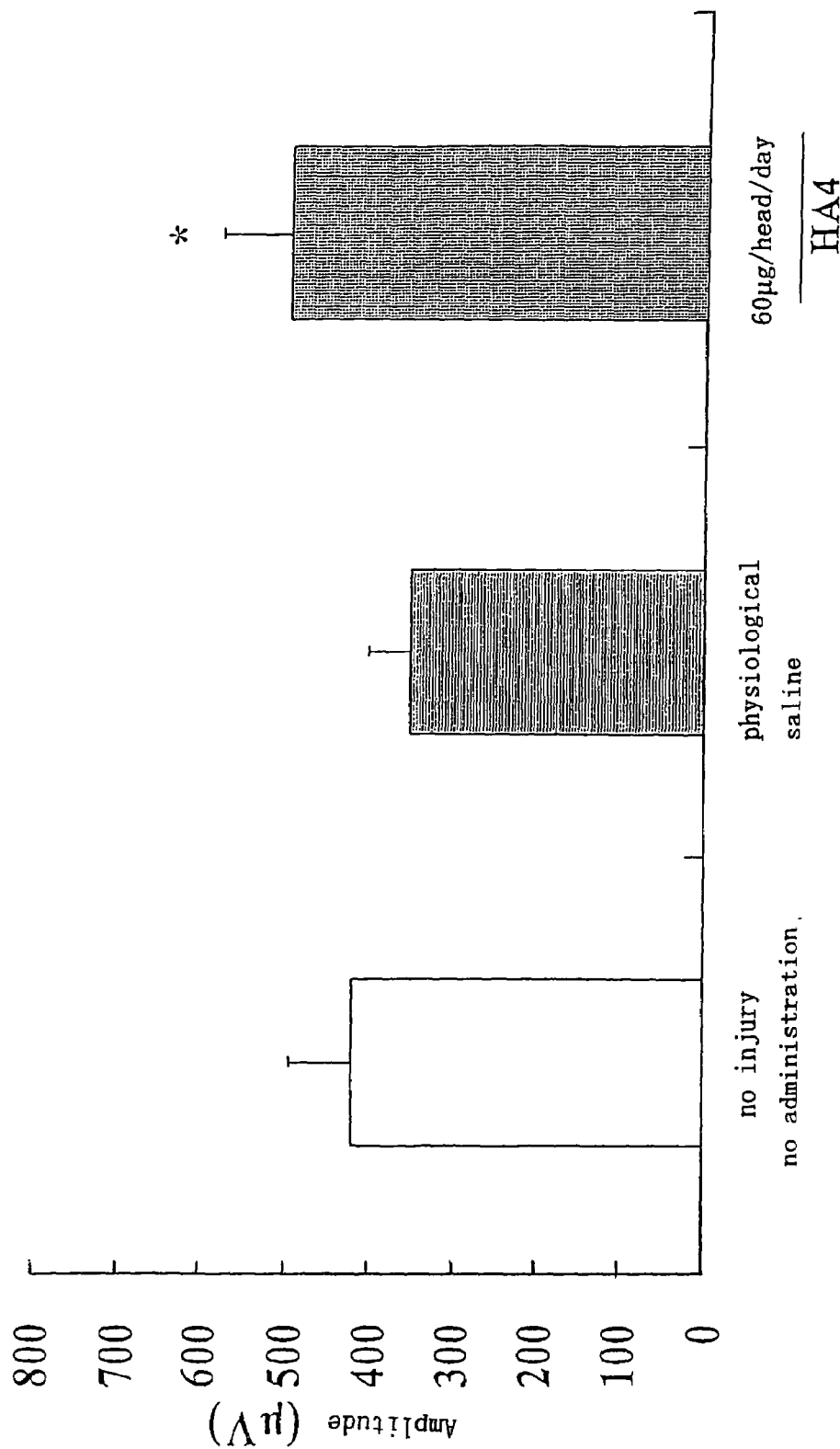
FIG. 3 is a graph illustrating the results of SCEP measurement in slightly injured models administered with HA4. The symbol "*" in this graph represents the significant difference of $p<0.05$ against the physiological saline-administered group (Dunnett's multiple comparison test).
Figure 4:
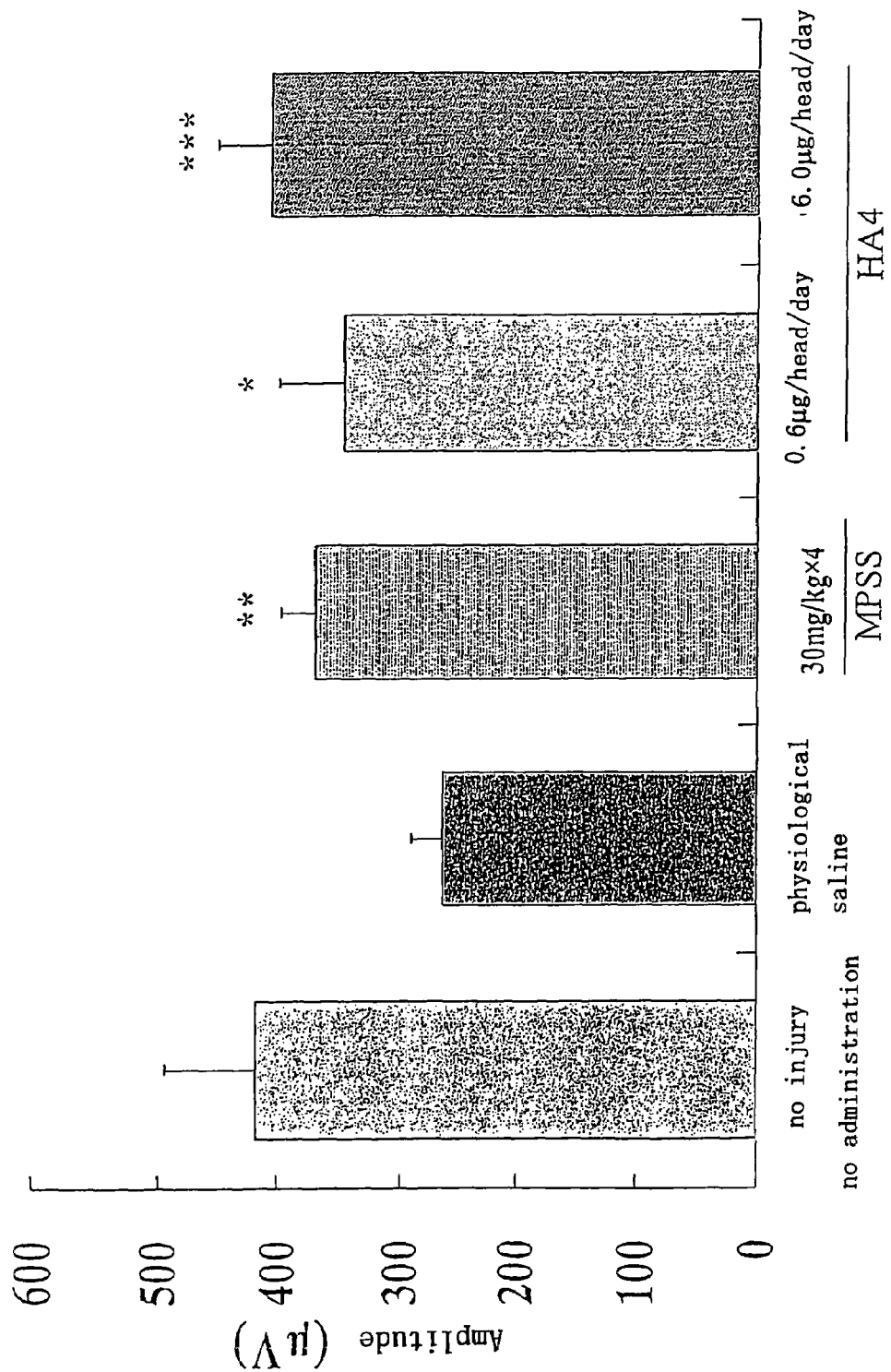
FIG. 4 is a graph illustrating the results of SCEP measurement in seriously injured models (I) administered with HA4. MPSS shows the methylprednisolone sodium succinate-administered group. The symbols "*", "", "*" in this graph represent the significant difference of $p<0.05$, $p<0.01$, $p<0.0001$, respectively, against the physiological saline-administered group (Dunnett's multiple comparison test).

7 days after the spinal cord injury, the spinal cord evoked potentials were determined. A tube was inserted into the windpipe under halothane anesthesia (initial time 4.0%, maintenance time 1.0) and stabilized with a muscle relaxant. Then, the head was fixed in the prone position, and the rat was maintained by a respirator. A catheter electrode was inserted between the second/third cervical vertebra and between the thirteenth thoracic vertebra/the first lumbar vertebra and supramaximal stimulus (stimulus frequency: 1 Hz, duration: 0.05 msec) was applied by means of an electromyograph (Powerpoint; manufactured by DANTEC DYNAMICS). Then, the spinal cord evoked potential (SCEP) was measured, and the "mean±SD" was calculated. The resultant potentials were evaluated using the amplitude of the first potential as an indicator. FIGS. 3 and 4 show the results of the slightly injured models and the results of the seriously injured models, respectively. The symbols "*" in those graphs represent the significant difference of $p<0.05$ against the physiological saline-administered group (Dunnett's multiple comparison test).

Figure 5:
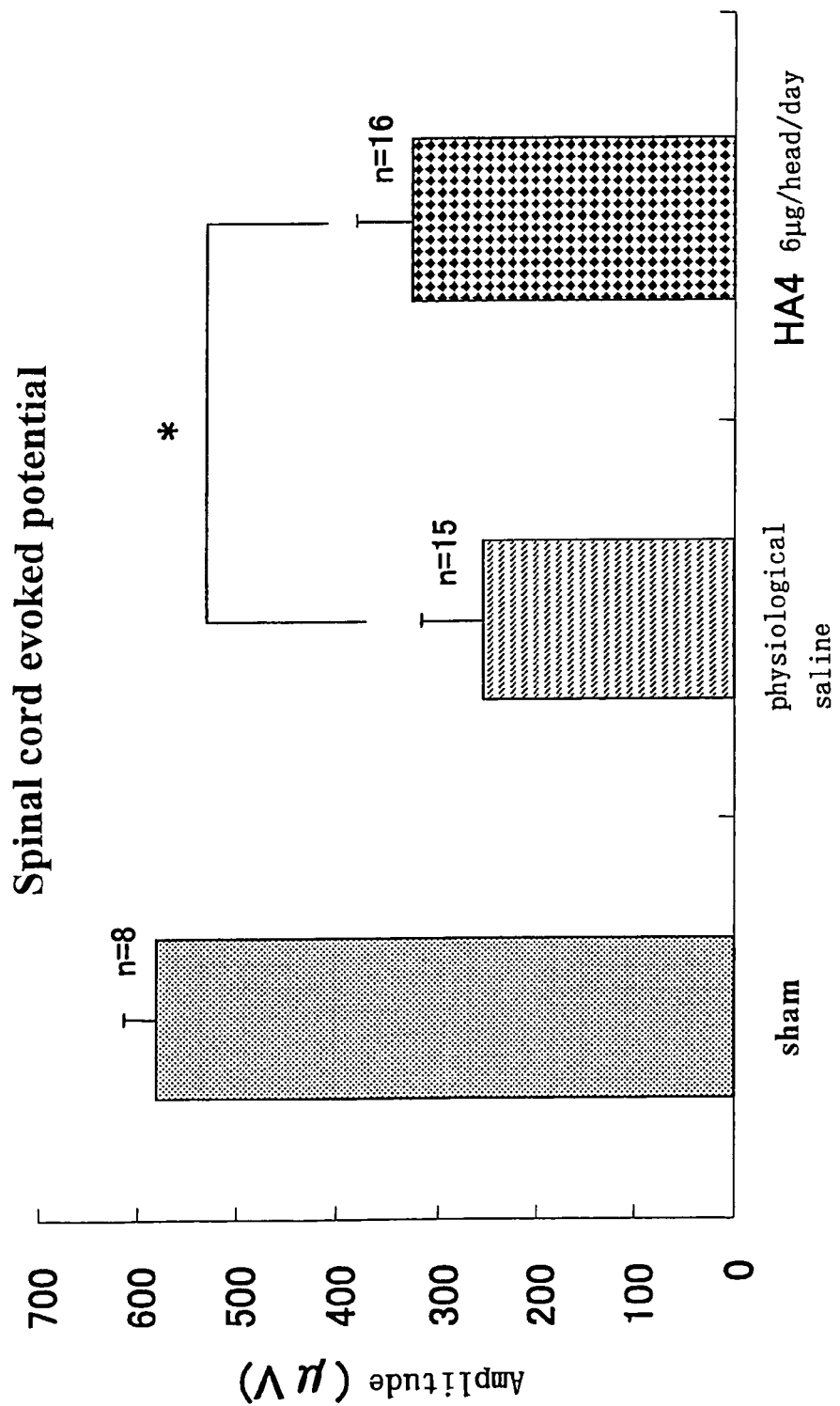
FIG. 5 is a graph illustrating the results of SCEP measurement in severely injured models (II). The symbol "*" in this graph represents the significant difference of $p<0.05$, against the physiological saline-administered group (Tukey's multiple comparison test).

As a result, in the case of the slightly injured models, the decrease of SCEP amplitude was significantly attenuated or the SCEP amplitude was recovered ($p<0.05$) in the HA4 (60 µg/animal/day)-administered group compared with the PBS-administered group. The level was the same as the normal level (no injury-no treatment group)(FIG. 3). In the case of the seriously injured models, the decrease of the SCEP amplitude was significantly attenuated or the SCEP amplitude was recovered in both HA4 (0.6 µg/animal/day)-administered group and HA4 (6 µg/animal/day)-administered group ($p<0.05$ and $p<0.001$, respectively; the same level as the normal level) compared with the PBS-administered group, and the HA4 (6 µg/animal/day)-administered group was found to have a stronger effect than that of MPSS (FIG. 4). Meanwhile, in the case of the seriously injured model (II), SCEP was measured in the same way as described above. The results are shown in FIG. 5. As a result, it was confirmed that the SCEP amplitude in the HA4 (6.0 µg/animal/day)-administered group was significantly recovered ($p<0.05$) compared with the physiological saline-administered group (FIG. 5). The symbol "*" in this graph represents the significant difference of $p<0.05$ against the physiological saline-administered group (Tukey's multiple comparison test).

(4) Evaluation from Histopathologic Viewpoint (Slightly Injured Model)

Figure 6:
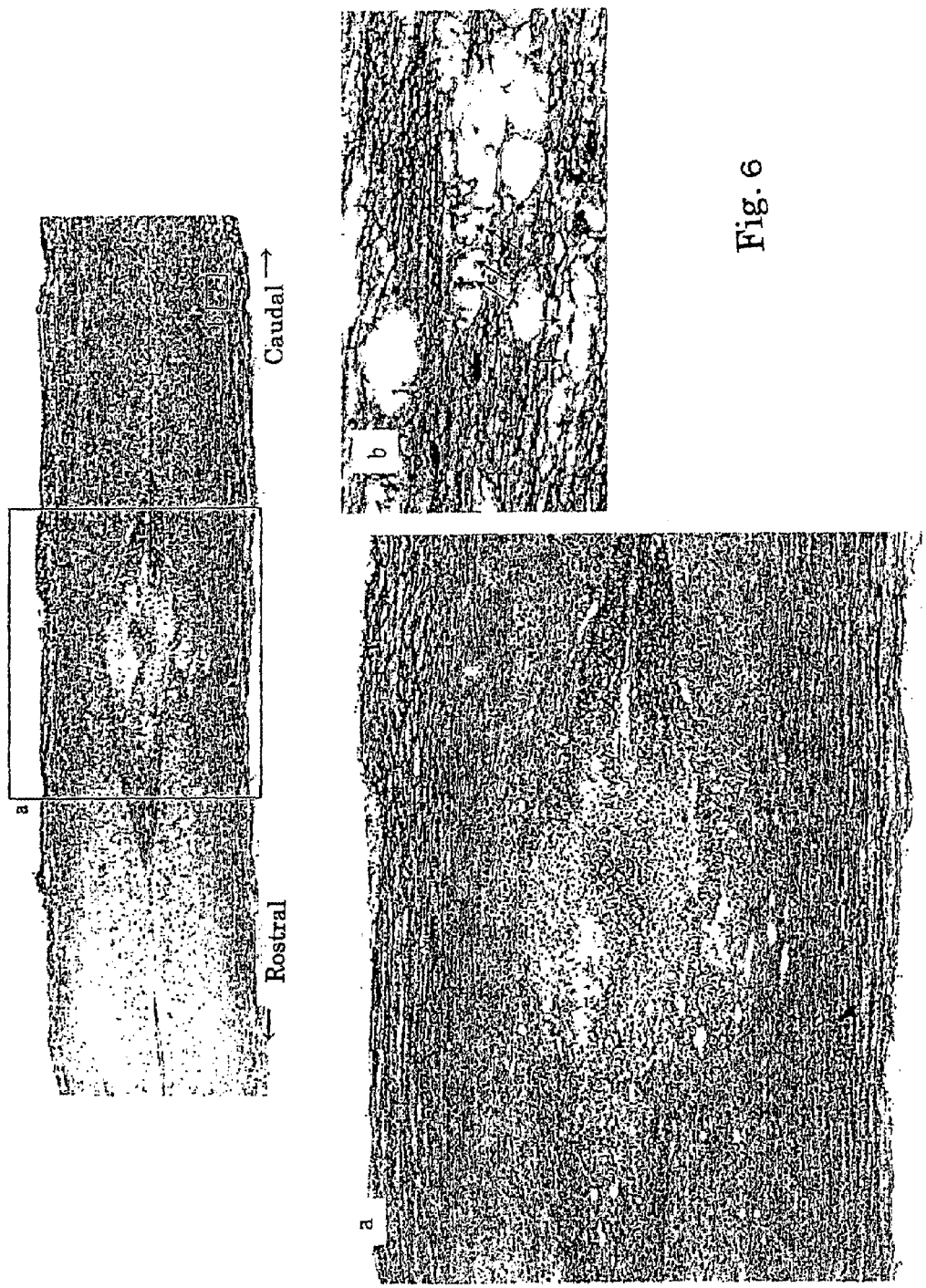
FIG. 6 is diagrams (photographs) illustrating the result of observations of the injured site in the PBS-administered group of slightly injured models. The arrows in the photograph "b" show loss of myelin.
Figure 7:
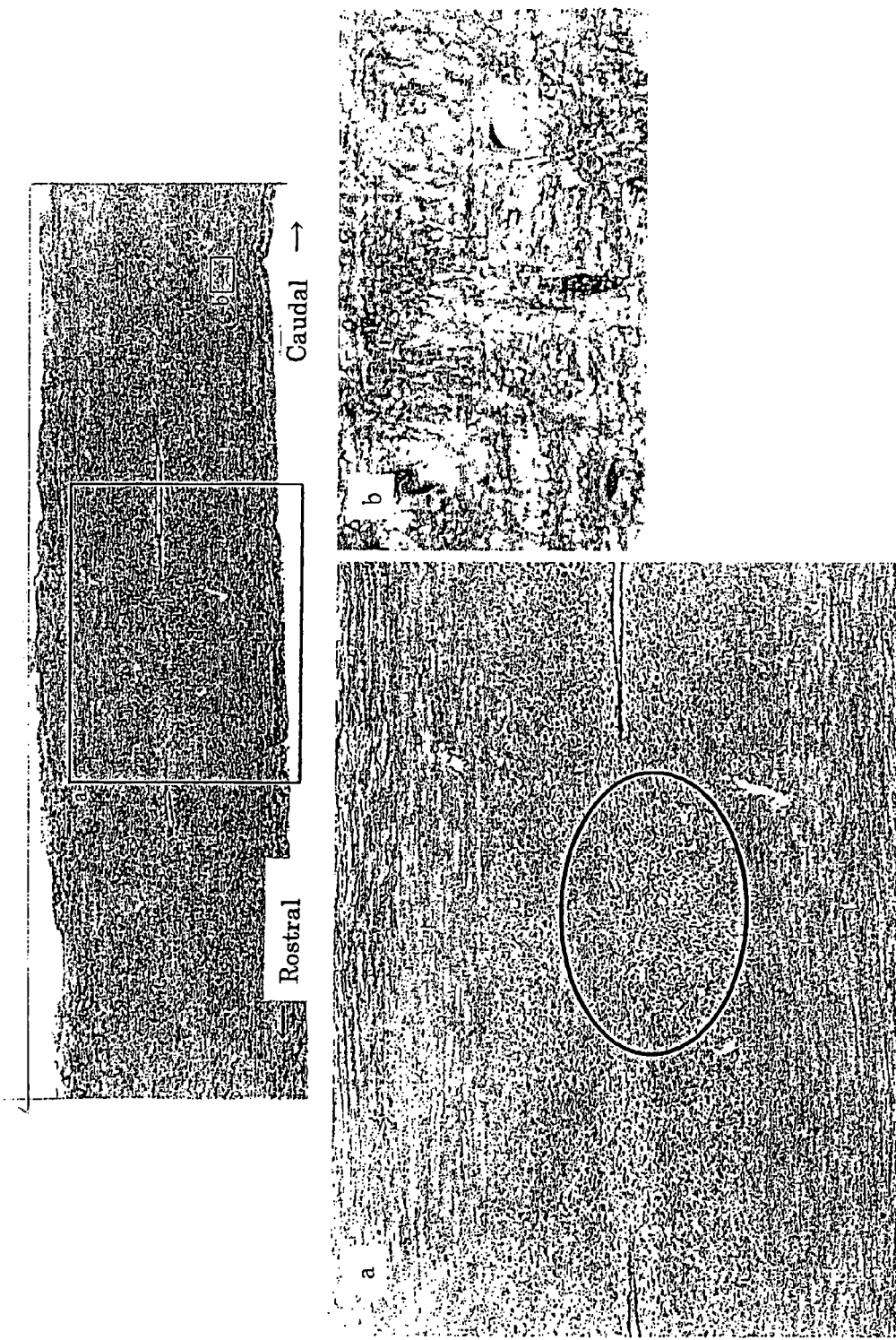
FIG. 7 is diagrams (photographs) illustrating the result of observations of the injured site in the HA4-administered group of slightly injured models. The ellipse represents the injured site.

A portion of the spinal cord having a length of about 2 cm around an injured site was fixed with neutral buffered formalin and then embedded in paraffin. Serial sections having coronal planes were prepared from the dorsal, and Kluver-Barrera staining was performed in which myelin was stained blue. In a tissue specimen at the position including the central canal, (a) the injured site region and (b) axons crossing from white matter to gray matter (axons entering in and leaving from the sixth thoracic spinal cord) were observed. FIGS. 6 and 7 show the results of the PBS-administered group and the HA-administered group, respectively.

As a result, in the tissue injured region of the PBS-administered group, edema and myelin loss were observed not only in the injured site (injured site) but also in white matter far from the injured site by 1 cm or more (FIG. 6). The sequential or scattered pattern represents the tissue damage in white matter (FIG. 6). For the HA4-administered group, the tissue injury was present only near the injured site, and edema and myelin loss were rarely observed in white matter (FIG. 7).

Figure 8:
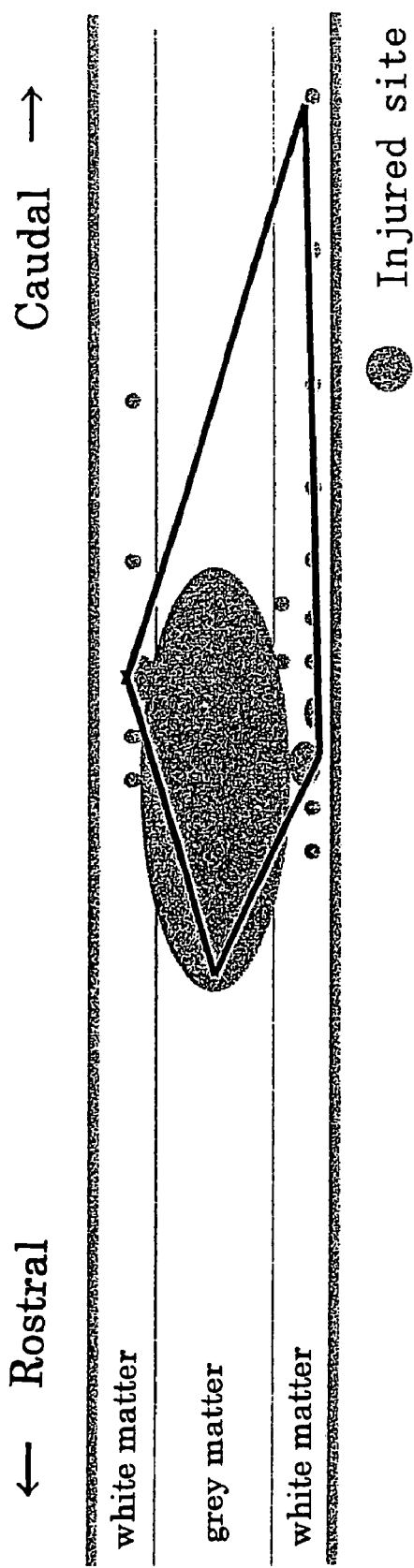
FIG. 8 is a scheme illustrating a measurement method of the injured region.
Figure 9:
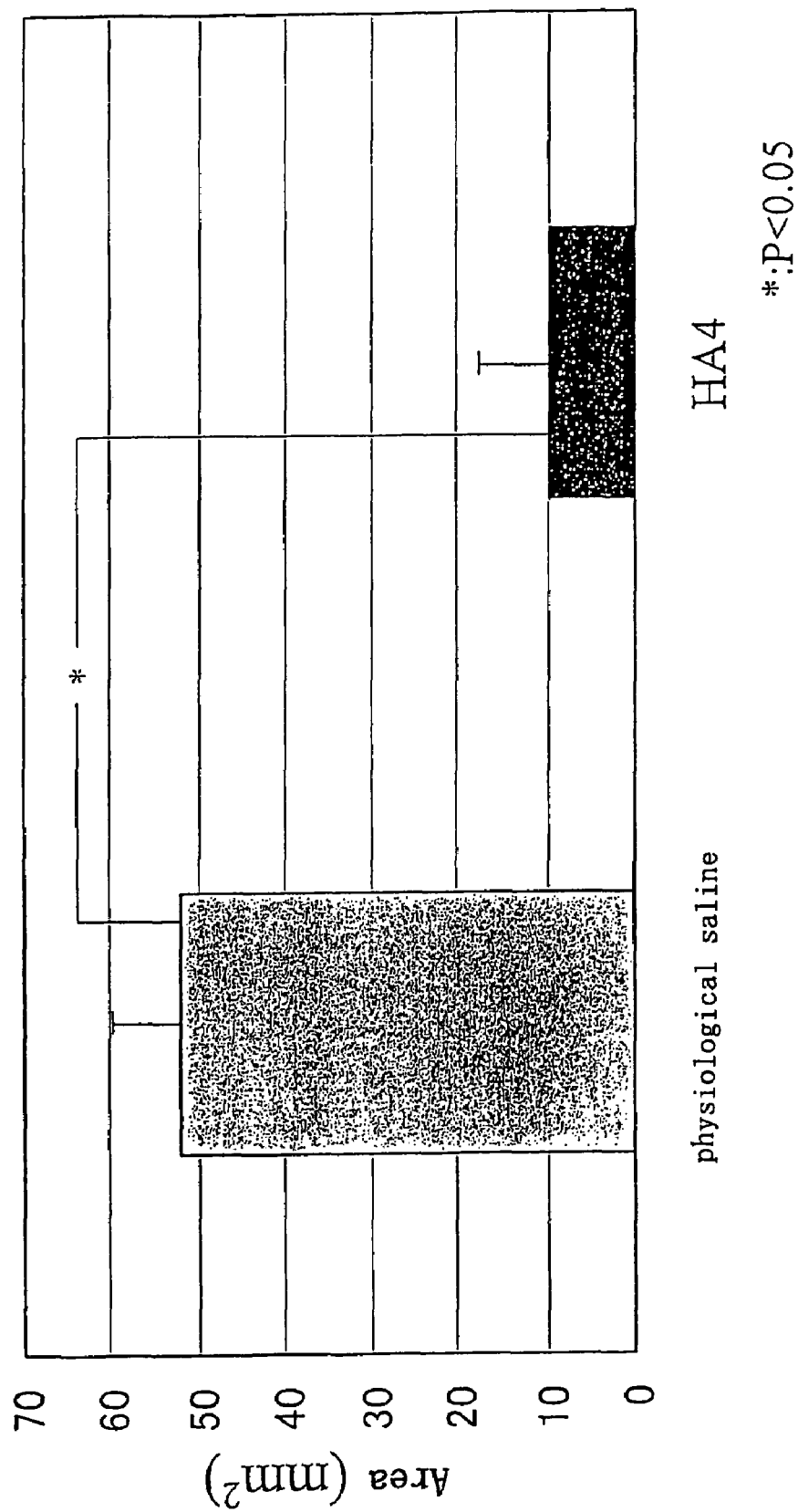
FIG. 9 is a graph illustrating measurement results of the "injured region" in the slightly injured models administered with HA4.

As shown in FIG. 8, in the plane including the central canal in the coronal, a square area within the four damage points on both sides and distant sides including the rostral point and the caudal point (the solid frame in FIG. 8) was defined as "injured area", and the damaged area was determined. As a result, the area of the HA4-administered group was significantly smaller than that of the PBS-administered group (FIG. 9).

Figure 10:
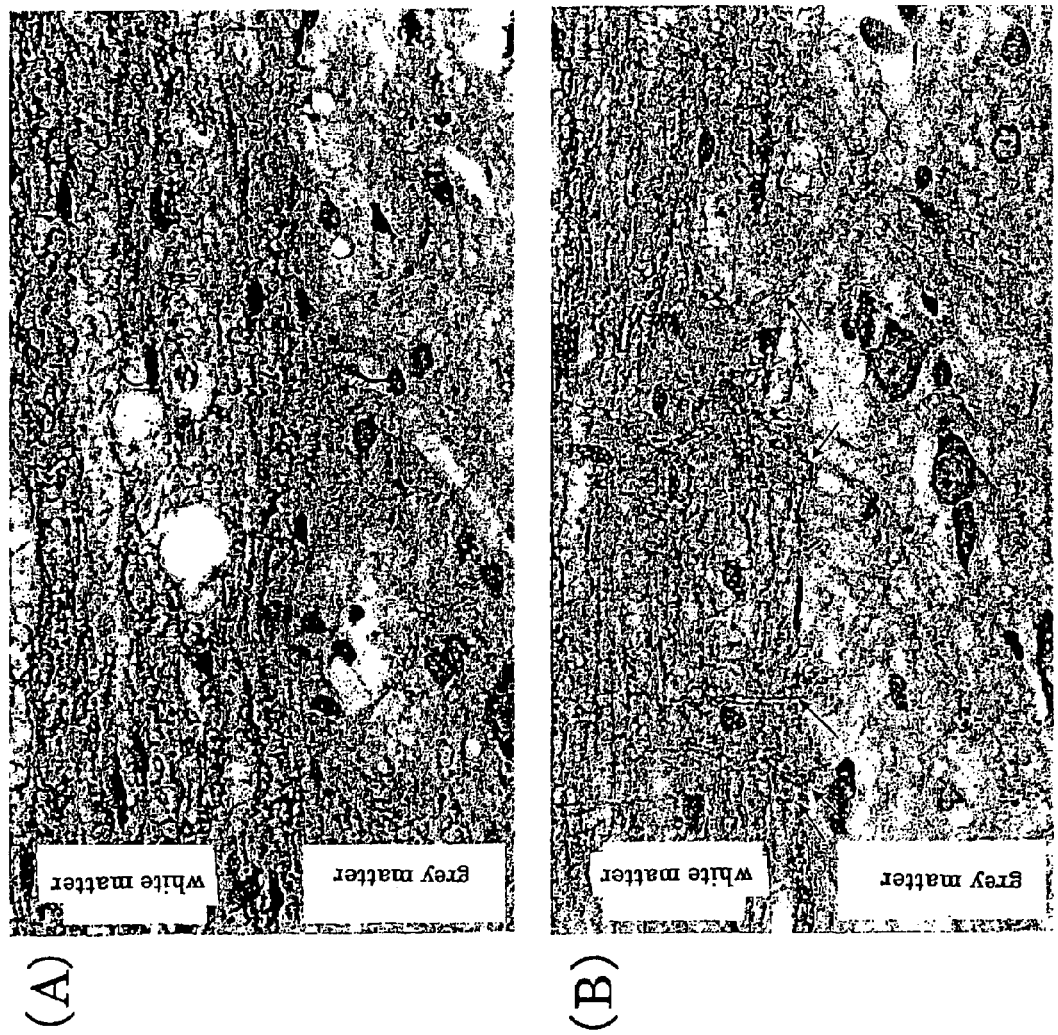
FIG. 10 is diagrams (photographs) illustrating the result of observations of the crossing portion from white matter to gray matter. The photographs (A) and (B) show the physiological saline-administered group and the HA4-administered group, respectively. The arrows represent axons crossing from white matter to gray matter.
Figure 11:
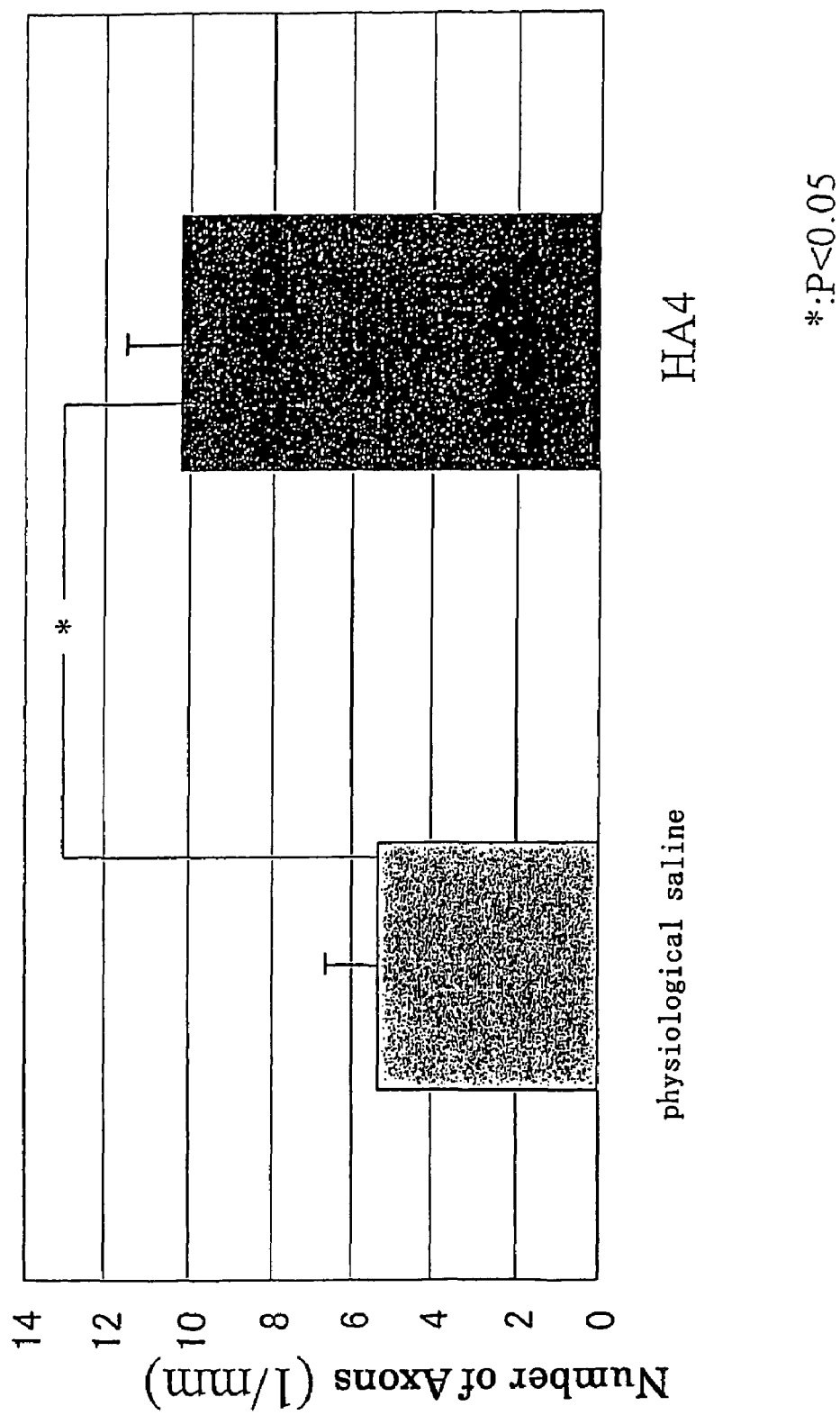
FIG. 11 is a graph illustrating measurement results of the number of axons crossing (intersecting) from white matter to gray matter in the slightly injured models.

Meanwhile, the number of the axons crossing (intersecting) from white matter to gray matter (the 5 mm range in the rostral/caudal direction in the injured site) was determined, and as a result, the number of axons in the HA4-administered group was significantly larger than that in the physiological saline-administered group (FIGS. 10 and 11).

(5) Evaluation from Praxiologic Viewpoint (Severely Injured Model (II))

Figure 12:
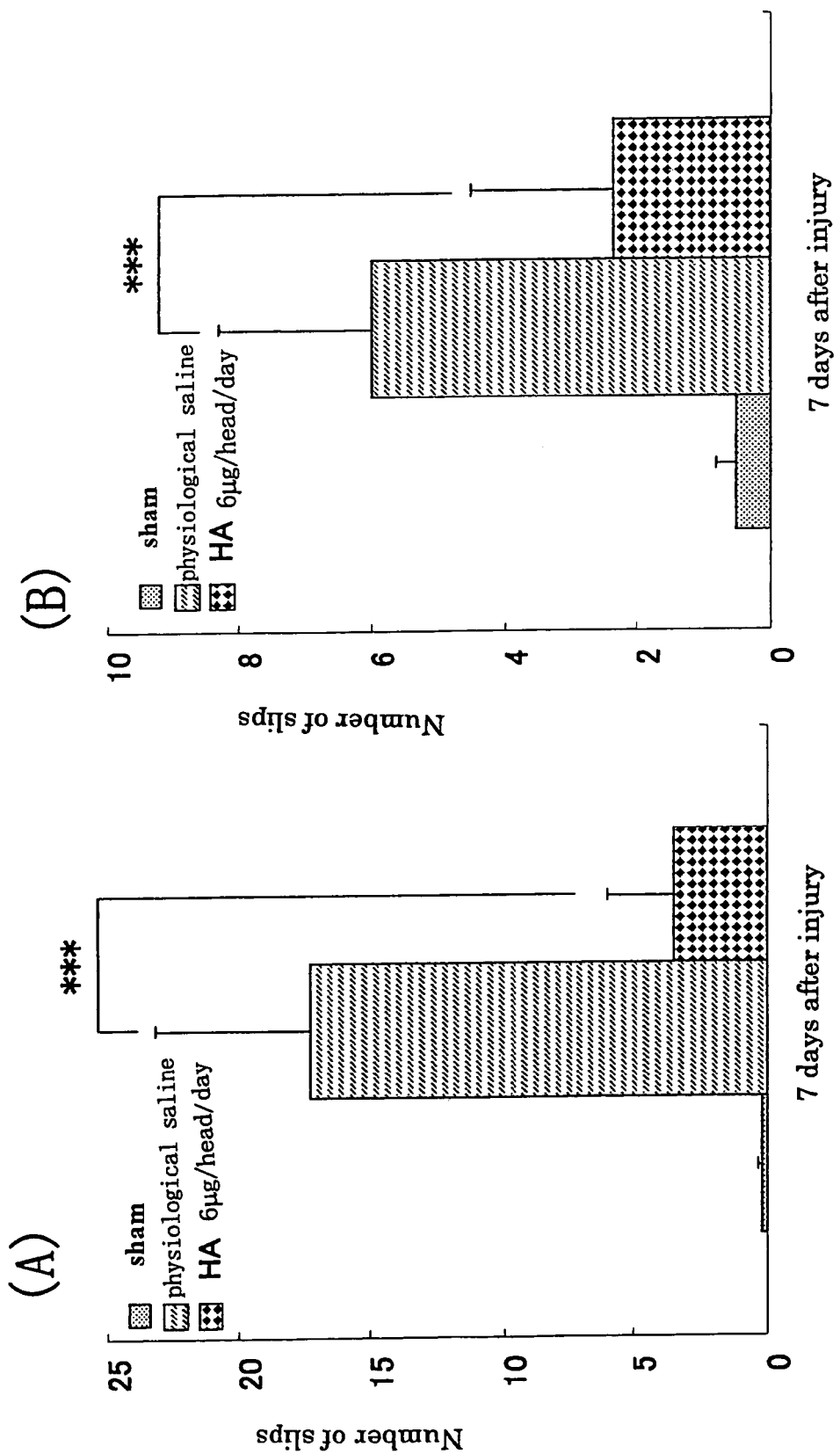
FIG. 12 is graphs illustrating measurement results of the numbers of slips in the hind limb 7 days after the spinal cord injury in severely injured models (II). The graphs (A) and (B)

Animals were trained for 5 to 7 days by crossing tests using a balance beam (3 cm×100 cm) and metal gauze (20 cm×100 cm) before the introduction of spinal cord injury. After completion of the training, a spinal cord severely injured model (II) was prepared for each animal in the same way as described in the above (1)-3. Thereafter, PBS or HA4 was interperitoneally continuously administered for 7 days, and each animal was allowed to cross on both obstacles four times. Then, the numbers of slips in the hind limb were recorded, and evaluated by the mean value (FIG. 12). As for the sham surgery group prepared by making a small incision in the dura mater (Sham), the number of slips in the hind limb was also determined.

Meanwhile, after the spinal cord injury, motor function tests in the hind limb were daily performed for 7 days in the PBS- or HA4-administered group and the sham surgery group. According to the method described by Basso et al., two test examiners individually evaluated blindly using the Basso-Beeattie-Bresnahan (BBB) scale, and the mean values were defined as the final score (FIG. 13).

In a balance beam or metal gauze crossing, the number of slips in the hind limb caused by both obstacles was found to be significantly low ($P<0.0001$)(FIG. 12), while in the motor function tests in the hind limb using the BBB scale, the motor function in the hind limb of the HA4 (6 µg/day)-administered group was found to be significantly recovered ($P<0.0001$) over 1 to 7 days after the spinal cord injury compared with the physiological saline-administered group (FIG. 13). The symbols "***" in this graph represent the significant difference of $p<0.0001$ against the physiological saline-administered group (Tukey's multiple comparison test).

The above-described results revealed that the HA4 administration suppressed the decrease of the spinal cord evoked potential or recovered the spinal cord evoked potential. The results show that HA4 has a suppressing effect on decrease of a nervous function caused by the spinal cord injury or recovering effect on a nerve function. Actually, it was confirmed that the motor function of the hind limb was significantly recovered in the HA4-administered group.

In the histopathologic evaluation, the tissue damage was suppressed in the HA4-administered group, and it is suggested that the effect of HA4 on the nerve function is associated with the suppression of the tissue damage. In particular, it was revealed that the suppression of myelin loss (demyelination in the secondary injury) and suppression of the reduction in axon number (the axons were considered to disappear due to apoptosis of neurocytes or oligodendrocytes caused by injury) by HA4 were closely related to the suppression of lowering of the nerve function by HA4.

Meanwhile, the results of the above-described tests using animals support the safety of the therapeutic agent of the present invention.

The above-described results revealed that the "low-molecular-weight HA" (in particular, HA4), which is "a low-molecular-weight saccharide composed of at least GlcA and/or GlcNAc", or a pharmaceutically acceptable salt thereof is extremely useful in treatment of nerve damage (in particular, nerve trauma or spinal cord injury.) and very safe.

INDUSTRIAL APPLICABILITY

The therapeutic agent of the present invention is very useful because it exerts an excellent effect on nerve damage, in particular, on nerve damage caused by spinal cord injury or nerve trauma, and is safely used.

What is claimed is:

1. A method of treating nerve damage, comprising administering an effective amount of a hyaluronic acid oligosaccharide or a pharmaceutically acceptable salt thereof to an animal suffering from nerve damage, wherein the hyaluronic acid oligosaccharide is selected from hyaluronic acid disaccharide to hyaluronic acid 50-saccharide.

2. The method according to claim 1, wherein nerve damage is caused by spinal cord injury or nerve trauma.

3. A method of recovering a nervous function lost due to a spinal cord injury comprising administering an effective amount of a hyaluronic acid oligosaccharide or a pharmaceutically acceptable salt thereof to an animal suffering from loss of nervous function, wherein the hyaluronic acid oligosaccharide is selected from hyaluronic acid disaccharide to hyaluronic acid 50-saccharide.

4. The method according to claim 1, wherein the nerve damage is selected from the group consisting of a decrease of a nervous function, demyelination, an edema in white matter, a reduction in axon number and tissue damage caused by a spinal cord injury or nerve trauma.

5. The method according to claim 1, wherein the hyaluronic acid oligosaccharide is hyaluronic acid tetrasaccharide.

6. The method according to claim 2, wherein the hyaluronic acid oligosaccharide is hyaluronic acid tetrasaccharide.

7. The method according to claim 3, wherein the hyaluronic acid oligosaccharide is hyaluronic acid tetrasaccharide.

8. The method according to claim 4, wherein the hyaluronic acid oligosaccharide is hyaluronic acid tetrasaccharide.

* * * * *